United States Patent [19]

Arbogast et al.

[11] Patent Number: 5,959,104
[45] Date of Patent: *Sep. 28, 1999

[54] N-ALKYL AMMONIUM ACETONITRILE BLEACH ACTIVATORS

[75] Inventors: James W. Arbogast, Dublin; James E. Deline, Livermore; Lafayette D. Foland, Dublin; Thomas W. Kaaret, Alamo; Kevin A. Klotter, Livermore; Michael J. Petrin, Antioch; William L. Smith; Alfred G. Zielske, both of Pleasanton, all of Calif.

[73] Assignee: The Clorox Company, Oakland, Calif.

[*] Notice: This patent is subject to a terminal disclaimer.

[21] Appl. No.: 09/059,607

[22] Filed: Apr. 13, 1998

Related U.S. Application Data

[63] Continuation of application No. 08/475,292, Jun. 7, 1995, Pat. No. 5,739,327.

[51] Int. Cl.⁶ ............ C07D 265/30; C07D 295/00; C07D 295/15; C09K 3/00
[52] U.S. Cl. ............. 544/163; 544/86; 544/402; 510/312; 252/186.39
[58] Field of Search ............. 544/163, 402, 544/86; 252/186.39, 186.38; 510/312

[56] References Cited

U.S. PATENT DOCUMENTS

| | | | |
|---|---|---|---|
| 2,425,693 | 8/1947 | Cook et al. ............. | 558/459 |
| 2,489,950 | 11/1949 | Blicke ............. | 546/205 |
| 2,625,547 | 1/1953 | Lawson et al. ............. | 544/171 |
| 2,774,758 | 12/1956 | Yanko ............. | 544/163 |
| 2,848,450 | 8/1958 | Rudner et al. ............. | 544/163 |
| 2,851,458 | 9/1958 | Billinghurst ............. | 594/163 |
| 2,868,786 | 1/1959 | Siemer et al. ............. | 544/171 |
| 3,532,735 | 10/1970 | Morgan ............. | 558/455 |
| 3,689,470 | 9/1972 | Shachat et al. ............. | 526/312 |
| 3,772,275 | 11/1973 | Hernestam et al. ............. | 544/163 |
| 3,780,092 | 12/1973 | Samour et al. ............. | 560/222 |
| 3,873,583 | 3/1975 | Walz et al. ............. | 554/103 |
| 3,882,035 | 5/1975 | Loffelman et al. ............. | 510/313 |
| 4,080,617 | 3/1978 | Kravetz et al. ............. | 510/314 |
| 4,134,889 | 1/1979 | Distler et al. ............. | 546/230 |
| 4,164,511 | 8/1979 | Distler et al. ............. | 558/346 |
| 4,199,466 | 4/1980 | Benson, Jr. ............. | 510/314 |
| 4,215,003 | 7/1980 | Finley et al. ............. | 8/111 |
| 4,328,226 | 5/1982 | Witek et al. ............. | 514/239.5 |
| 4,342,872 | 8/1982 | Grier et al. ............. | 546/186 |
| 4,397,757 | 8/1983 | Bright et al. ............. | 252/186.41 |
| 4,551,526 | 11/1985 | Mai et al. ............. | 544/163 |
| 4,737,498 | 4/1988 | Banasiak et al. ............. | 514/237.8 |
| 4,751,015 | 6/1988 | Humphreys et al. ............. | 544/139 |
| 4,904,406 | 2/1990 | Darwent et al. ............. | 510/376 |
| 4,915,863 | 4/1990 | Aoyagi et al. ............. | 510/376 |
| 4,921,631 | 5/1990 | Gradwell et al. ............. | 252/186.38 |
| 4,978,770 | 12/1990 | Aoyagi et al. ............. | 558/455 |
| 5,093,022 | 3/1992 | Sotoya et al. ............. | 510/376 |
| 5,106,528 | 4/1992 | Francis et al. ............. | 252/186.23 |
| 5,236,616 | 8/1993 | Oakes et al. ............. | 510/376 |
| 5,281,361 | 1/1994 | Adams et al. ............. | 252/186.38 |
| 5,330,677 | 7/1994 | Sotoya et al. ............. | 252/186.38 |
| 5,399,746 | 3/1995 | Steiger et al. ............. | 560/251 |
| 5,405,412 | 4/1995 | Willey et al. ............. | 8/111 |
| 5,460,747 | 10/1995 | Gosselink et al. ............. | 252/186.38 |
| 5,591,378 | 1/1997 | Deline et al. ............. | 252/186.38 |

FOREIGN PATENT DOCUMENTS

| | | |
|---|---|---|
| 883075582 | 8/1988 | European Pat. Off. . |
| A20303520 | 8/1988 | European Pat. Off. . |
| 912011707 | 5/1991 | European Pat. Off. . |
| 912012606 | 5/1991 | European Pat. Off. . |
| 0790244 | 2/1997 | European Pat. Off. . |
| 0 790 244 A1 | 8/1997 | European Pat. Off. . |
| P25035829 | 1/1975 | Germany . |
| P25557691 | 12/1975 | Germany . |
| P26204455 | 5/1976 | Germany . |
| 62-225871 | 9/1987 | Japan . |
| 63-167157 | 7/1988 | Japan . |
| 1-230773 | 9/1989 | Japan . |
| 6136391 | 10/1992 | Japan . |
| 96/07650 | 3/1996 | WIPO . |

OTHER PUBLICATIONS

Hart et al., "Some New Quaternary–Substituted Alkyl Morpholinium Chlorides and Pyrrolidinium Alkyl Sulfates," *Journal of Organic Chemistry*, 22:1 (Mar. 5, 1957), pp. 86–88.

Gubanova et al., "Synthesis and Antiviral Activity of Organic and Organophosphorus Derivatives of α–Aminonitriles," translated from *Khimiko–farmatsevticheskii Zhurnal*, 26, No. 7–8, pp. 60–62 (1992).

Stanley et al., "Synthesis and Enzymatic Evaluation of Some N–Alkyl Branched Chain Piperidine Salts and N–Alkyl–3–(N,N–diethylcarbamoyl)piperidine Salts as Inhibitors of Acetyl– and Butyrylcholinesterase," *J. Medicinal Chemistry*, 17, No. 1, (1974).

Lespagnol et al., "Guanidines monosubstituées à fonction ammonium quaternaire," *Mèmoires Prèsentès a la Sociètè Chimique*, paper presented at the Congress of the International Pharmaceutical Federation, Zurich, Sep. 1959. (English Translation).

*Primary Examiner*—Joseph D. Anthony
*Attorney, Agent, or Firm*—Majestic, Parsons, Siebert & Hsue

[57] ABSTRACT

Bleaching compositions are provided that comprise a nitrile containing compound that has the nitrile bonded to a quaternary nitrogen through a methylene unit (where one or both of the normal hydrogens can be substituted), and two of the quaternary nitrogen bonds are part of a saturated ring. This saturated ring contains from two to eight atoms in addition to the quaternary nitrogen. A source of active oxygen will react with the nitrile for bleaching applications. Particularly preferred nitrile containing compounds are N-alkyl morpholinium acetonitrile salts.

1 Claim, No Drawings

N-ALKYL AMMONIUM ACETONITRILE BLEACH ACTIVATORS

This is a continuation of application Ser. No. 08/475,292, filed Jun. 7 1995, now U.S. Pat. No. 5,739,327 entitled "N-ALKYL AMMONIUM ACETONITRILE BLEACH ACTIVATORS".

FIELD OF THE INVENTION

The present invention generally relates to N-alkyl ammonium acetonitrile compounds, and particularly for use as activators for hydrogen peroxide in bleaching and cleaning applications.

BACKGROUND OF THE INVENTION

Peroxy compounds are effective bleaching agents, and compositions including mono- or di-peroxyacid compounds are useful for industrial or home laundering operations. For example, U.S. Pat. No. 3,996,152, issued Dec. 7, 1976, inventors Edwards et al., discloses bleaching compositions including peroxygen compounds such as diperazelaic acid and diperisophthalic acid.

Peroxyacids (also known as "peracids") have typically been prepared by the reaction of carboxylic acids with hydrogen peroxide in the presence of sulfuric acid. For example, U.S. Pat. No. 4,337,213, inventors Marynowski et al., issued Jun. 29, 1982, discloses a method for making diperoxyacids in which a high solids throughput may be achieved.

However, granular bleaching products containing peroxyacid compounds tend to lose bleaching activity during storage, due to decomposition of the peroxyacid. The relative instability of peroxyacid can present a problem of storage stability for compositions consisting of or including peroxyacids.

One approach to the problem of reduced bleaching activity of peroxyacid compositions has been to include activators of peroxyacids. U.S. Pat. No. 4,283,301, inventor Diehl, issued Aug. 11, 1981, discloses bleaching compositions including peroxygen bleaching compounds, such as sodium perborate monohydrate or sodium perborate tetrahydrate, and activator compounds such as isopropenyl hexanoate and hexanoyl malonic acid diethyl ester.

U.S. Pat. No. 4,778,618, Fong et al., issued Oct. 18, 1988 provides novel bleaching compositions comprising peracid precursors with the general structure

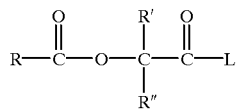

wherein R is $C_{1-20}$ linear or branched alkyl, alkylethoxylated, cycloalkyl, aryl, substituted aryl; R' and R" are independently H, $C_{1-20}$ alkyl, aryl, $C_{1-20}$ alkylaryl, substituted aryl, and $N^+R_3^\alpha$, wherein $R^\alpha$ is $C_{1-30}$ alkyl; and where L is a leaving group which can be displaced in a peroxygen bleaching solution by peroxide anion. U.S. Pat. No. 5,182,045, issued Jan. 26, 1993, and U.S. Pat. No. 5,391,812, issued Feb. 21, 1995, inventors Rowland et al. are similar, but are polyglycolates of the Fong et al. monoglycolate precursors, or activators.

U.S. Pat. No. 4,915,863, issued Apr. 10, 1990, inventors Aoyagi et al., discloses compounds said to be peracid precursors that have nitrile moieties. U.S. Pat. No. 5,236,616, issued Aug. 17, 1993, inventors Oakes et al., discloses compounds said to be cationic peroxyacid precursors that have nitrile moieties. These nitrile containing activators do not contain a leaving group, such as the Fong et al. leaving groups, but instead include a quaternary ammonium group suggested as activating the nitrile and said, upon hydrolysis in the presence of hydrogen peroxide, to generate a peroxy imidic acid as bleaching species. The Aoyagi et al. activators include an aromatic ring, which tends to cause fabric yellowing.

Thus, new peroxygen activators that do not gray or harm fabrics and that provide superior bleaching remain desirable for laundry and household bleaching and cleaning applications, such as laundry detergents, laundry bleaches, hard surface cleaners, toilet bowl cleaners, automatic dishwashing compositions, and the like.

SUMMARY OF THE INVENTION

In one aspect of the present invention, novel compounds are provided that have the Formula I (A and B) structure:

FORMULA IA

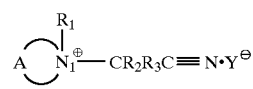

FORMULA IB

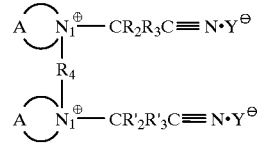

In the general Formula I structure (with both A and B subparts), A is a saturated ring formed by a plurality of atoms in addition to the $N_1$ atom. The ring atoms include at least one carbon atom and at least one of O, S and N atoms. $R_2$ and $R_3$ are each H, a $C_{1-24}$ alkyl, cycloalkyl, or alkaryl, or a repeating or nonrepeating alkoxyl or alkoxylated alcohol where the alkoxy unit is $C_{2-4}$. "Y" is at least one counterion.

The Formula IA structure has a $R_1$ substituent bonded to the $N_1$ atom. The $R_1$ substituent includes either:

(a) a $C_{1-24}$ alkyl or alkoxylated alkyl where the alkoxy is $C_{2-4}$; a $C_{4-24}$ cycloalkyl; a $C_{7-24}$ alkaryl; or a repeating or nonrepeating alkoxy or alkoxylated alcohol, where the alkoxy unit is $C_{2-4}$;

or (b) —$CR_2R_3C\equiv N$ where $R_2$ and $R_3$ are each H, a $C_{1-24}$ alkyl, cycloalkyl, or alkaryl, or a repeating or nonrepeating alkoxyl or alkoxylated alcohol where the alkoxy unit is $C_{2-4}$.

The Formula IB dimer structure has $R_2'$ and $R_3'$ chosen from the same moieties as $R_2$ and $R_3$ and which may be the same as $R_2$ and $R_3$ or be different, and has a $R_4$ linking group bonded to the $N_1$ atom. The $R_4$ substituent includes a polyoxyalkylene group with 1 to 24 oxyalkylene units or an alkylene group with 1 to 24 carbons, as well as thioethers.

The Formula I compounds have a quaternary nitrogen atom ($N_1$) so at least one appropriate counterion (Y) will be associated therewith.

The novel compounds with the Formula I structure are particularly useful when formulated as compositions that include a source of active oxygen, and these compositions provide excellent bleaching in alkaline solutions without causing fabric yellowing.

Preferred embodiments of the invention include salts of N-methyl morpholinium acetonitrile, N-butyl morpholinium acetonitrile, N-hexyl morpholinium acetonitrile, and N-octyl morpholinium acetonitrile, which are illustrated by Formula II (with "n" being 0 to 23 and where "Y" is the at least one counterion).

FORMULA II

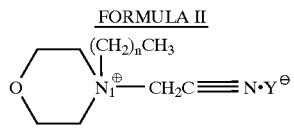

A particularly preferred embodiment of the invention is an N-methyl morpholinium acetonitrile salt (sometimes designated "MMA" where "n" of Formula II is 0) which has excellent stability, shows improved bleaching and cleaning performance when formulated with a source of active oxygen in alkaline wash water, and which causes no fabric graying.

In another aspect of the present invention, a bleaching composition comprises a source of active oxygen and a nitrile having the Formula IIIA structure:

FORMULA IIIA

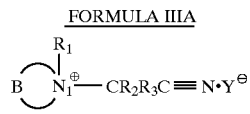

In the Formula IIIA structure, B is a saturated ring formed by a plurality of atoms in addition to the $N_1$ atom, and the ring atoms optionally include one or more of O, S and N atoms.

Formula IIIA is analogous to Formula I; however, the B saturated ring can be all carbons (except for the $N_1$ atom). As with the dimeric Formula IB, another aspect of this invention concerns a dimeric nitrile with a B saturated ring as just described.

In yet another aspect of this invention, a composition includes a nitrile containing compound, the nitrile bonded to a quaternary nitrogen through a methylene unit, two of the quaternary nitrogen bonds being part of a saturated ring. This nitrile containing compound is preferably formulated with a peroxide compound for bleaching applications.

Compositions of the invention are useful as or in laundry products, such as bleaching additives, detergents, detergent boosters, detergents with bleach, bleaches, bleaching aids, stain removers, and spot treatment products such as stain removers, prewash and presoak laundry aids. Among the advantages derived from compositions of the invention are improved cleaning, stain removal, spot removal, whitening, and brightening of treated articles without causing fabric yellowing.

DETAILED DESCRIPTION OF THE PREFERRED EMBODIMENTS

Compounds of the invention include certain nitrites having the structure illustrated by Formula I (A and B). The $N_1$ atom of the Formula I (both A and B subparts) compound is part of a saturated ring, illustrated by "A" in Formula I.

FORMULA IA

FORMULA IB

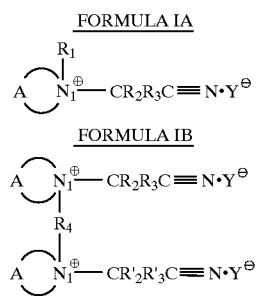

This saturated ring of which $N_1$ is a part has a plurality of atoms. The saturated ring illustrated by ring "A" in Formula I has at least one hetero atom in the saturated ring in addition to the $N_1$, preferably wherein the ring includes an oxygen atom, a sulfur atom, or one or two additional nitrogen atoms.

The at least one nitrogen in the saturated ring ($N_1$) shown in Formula I is N-acetonitrile substituted and also quaternized. Without being bound by theory, we believe that the electron withdrawing nature of the quaternary nitrogen may be increased by being part of a saturated, heterocyclic ring and may also function to improve the hydrophilic character of the oxidant.

A substituent $R_1$ will be bonded to the $N_1$ atom of the Formula IA structure and additionally a nitrile moiety ($-CR_2R_3C\equiv N$) is bonded to the $N_1$ atom, where $R_2$ and $R_3$ are each H, a $C_{1-24}$ alkyl, cycloalkyl, or alkaryl, or a repeating or nonrepeating alkoxyl or alkoxylated alcohol where the alkoxy unit is $C_{2-4}$. The $R_1$ substituent may be a $C_{1-24}$ alkyl or alkoxylated alkyl where the alkoxy is $C_{2-4}$, a $C_{4-24}$ cycloalkyl, a $C_{7-24}$ alkaryl, a repeating or nonrepeating alkoxy or alkoxylated alcohol, where the alkoxy unit is $C_{2-4}$, and illustrative such groups are, for example,

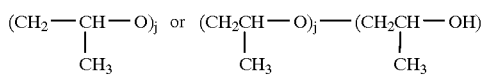

where j=1 to 24. The $R_1$ substituent may also be another $-CR_2R_3C\equiv N$, and again $R_2$ and $R_3$ are each H, a $C_{1-24}$ alkyl, cycloalkyl, or alkaryl, or a repeating or nonrepeating alkoxyl or alkoxylated alcohol where the alkoxy unit is $C_{2-4}$, and illustrative such groups are:

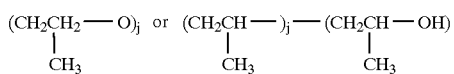

where j=1 to 24.

Formula IB illustrates dimeric embodiments of the invention where $R_4$ is a linking group. This linking group $R_4$ may be a polyoxyalkylene group with 1 to 24 oxyalkylene units, such as groups derived from ethylene oxide, propylene oxide, butylene oxide, or mixtures thereof. Examples are:

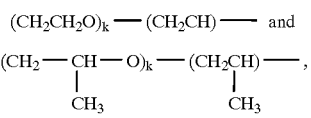

where k=1 to 24. Thioethers may also be used. The $R_4$ linking group may also be an alkylene group with 1 to 24 carbons. $R_2$ and $R_3$ are each H, a $C_{1-24}$ alkyl, cycloalkyl, or alkaryl, or a repeating or nonrepeating alkoxyl or alkoxylated alcohol where the alkoxy unit is $C_{2-4}$. $R_2'$ and $R_3'$ chosen from the same moieties as $R_2$ and $R_3$ and which may be the same as $R_2$ and $R_3$ or be different.

Particularly preferred, saturated rings forming the cyclic configuration A of Formula I contain six atoms including the $N_1$ atom, but the number of atoms forming the cyclic configuration can range from 3 to 9. When two heteroatoms are present with the cyclic configuration A of Formula I, then a three member ring is unusual; but, for the cyclic configuration B of Formula III shown below, where there may only be $N_1$ as the sole heteroatom, then three membered rings are very likely.

Particularly preferred activator embodiments are illustrated by Formula II (where "Y" is at least one counterion and "n" is 0 to 23.

FORMULA II

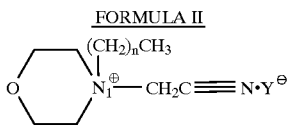

Compounds of the invention must have a saturated ring formed by the A or B atoms and the $N_1$ atom, since presence of an aromatic (unsaturated) ring has been found to cause undesirable fabric yellowing when the activators are combined with a source of active oxygen and used in bleaching applications.

Where the saturated ring A of the Formula I structure includes two N atoms, and then the second N atom, designated $N_2$, may be a secondary amine, a tertiary amine (having the substituent —$CR_5R_6CN$) or a quaternary amine (having the substituents —$R_5$ and —$CR_5R_6CN$), wherein $R_5$ and $R_6$ may each be a hydrogen or a $C_{1-6}$ alkyl.

Novel derivatives of the invention include peroxyimidic intermediates that are believed formed from the novel nitrites in the presence of a peroxygen source. So formed, peroxyimidic derivatives typically would be short-lived intermediates formed in situ when the nitrites of the invention interact with a source of hydrogen peroxide and where the reactive nitrile moiety forms a peroxyimidic acid. However, such peroxyimidic derivatives may also be prepared in isolatable, stable form by analogy to syntheses known in the art.

Counterions

Since compounds of the invention are typically quaternized, they will include at least one counterion (designated as "Y"), which can be substantially any organic or inorganic anion, such as, but not limited to, chloride, bromide, nitrate, alkyl sulfate, and the like. Dimeric activators (e.g. Formula IB) will include at least two counterions, or a doubly charged anion, such as sulfate, carbonate, and the like.

Bleaching and Cleaning Compositions

Bleaching and cleaning compositions of the invention include a nitrile as activator, together with a source of active oxygen. The nitrile activator of inventive compositions is represented by Formula III (A and B).

FORMULA IIIA

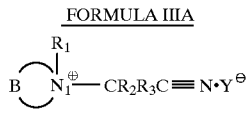

-continued

FORMULA IIIB

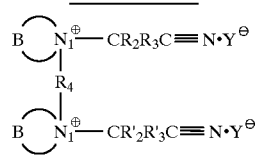

In Formula III, B is a saturated ring formed by a plurality of atoms in addition to the $N_1$ atom, and the ring atoms preferably include at least one carbon atom and at least one of O, S and N atoms, but can be composed of the one $N_1$ atom and the rest carbons. The $R_1$, $R_2$, $R_3$, $R_2'$, $R_3'$, $R_4$, $R_5$, and $R_6$ groups and the Y counterion are as previously described.

Most of the compounds having the Formula III structure are novel. In addition, compounds, for example, a N-methyl piperidinium acetonitrile salt, which is included in the Formula III structure, when combined with a source of active oxygen, constitute novel bleaching compositions.

Compounds having the Formula I and Formula III structures have a saturated ring formed by a plurality of atoms, broadly ranging from 3 to 9, although preferably containing 6 atoms including the $N_1$ atom. Preparation of these compounds will most conveniently start with a compound already having the formed ring. For example, a number of preparations of inventive nitrites hereinafter described will begin with morpholine (see, e.g., the Formula II structure). An example of three membered rings is aziridine, e.g., N-methylacetonitrile aziridinium; as an example of four membered rings there is azetidine, e.g., N-ethyl-acetonitrile azetidinium; as an example of five membered rings there is pyrrolidine, e.g., N-butylacetonitrile pyrrolidinium; as an example of six membered rings, in addition to morpholine, there is piperidine, e.g., N-methylacetonitrile piperidinium; as an example of seven membered rings there is homopiperidine, e.g., N-ethylacetonitrile homopiperidinium; as an example of eight membered rings there is tropane, e.g., N-methylacetonitrile-8-azabicyclo[3.2.1]octane; and, as an example of nine membered rings there is octahydroindole, e.g., N-methylacetonitrile octahydroindolinium.

The peroxide or active oxygen source for compositions of the invention may be selected from the alkaline earth metal salts of percarbonate, perborate, persilicate and hydrogen peroxide adducts and hydrogen peroxide. Most preferred are sodium percarbonate, sodium perborate mono- and tetrahydrate, and hydrogen peroxide. Other peroxygen sources may be possible, such as monopersulfates and monoperphosphates. In liquid applications, liquid hydrogen peroxide solutions are preferred, but the activator may need to be kept separate therefrom prior to combination in aqueous solution to prevent premature decomposition.

The range of peroxide to activator is preferably determined as a molar ratio of peroxide to activator. Thus, the range of peroxide to each activator is a molar ratio of from about 0.1:1 to 100:1, more preferably about 1:1 to 10:1 and most preferably about 2:1 to 8:1. This peracid activator/peroxide composition should provide about 0.5 to 100 ppm A.O., more preferably about 1 to 50 ppm peracid A.O. (active oxygen), and most preferably about 1 to 20 ppm peracid A.O., in aqueous media for typical laundry applications. Formulations intended for hard surface cleaning will more typically have peracid activator/peroxide providing from about 0.5 to 1,000 ppm A.O., more preferably about 1 to 500 ppm peracid A.O., and most preferably about 1 to 200 ppm peracid A.O.

Compositions of the invention have been found to provide superior bleaching (cleaning and stain removal) benefits on common laundry stains when compared to a prior known activator containing an aromatic ring (N-acetonitrile pyridinium chloride). Thus, Table 1 summarizes comparative data between two different compositions of the invention compared with the prior art, N-acetonitrile pyridinium chloride activator together with a source of active oxygen.

The experiment summarized by the data of Table 1 is more fully described by Example 5.

TABLE 1

|  | % Stain Removal, 8-Stain Average |
|---|---|
| Inventive Compositions |  |
| MMA Activator | 72.4 |
| BMA Activator | 73.6 |
| Prior Art Composition |  |
| PYACN Activator | 63.2 |

The "MMA" activator was the novel N-methyl morpholinium acetonitrile methyl sulfate, the novel "BMA" activator was N-butyl morpholinium acetonitrile chloride, and the prior art activator "PYACN" was N-acetonitrile pyridinium chloride. All three bleaching compositions included peroxide (in addition to the particular activator) supplied in the form of hydrogen peroxide by adding 0.11 milliliters of 30%stock to 1.5 liter wash volumes to give the equivalent of 25 ppm active oxygen.

The inventive compositions provide a substantial brightness (whiteness improvement due to bleaching) and whitening (lack of colored byproduct formation) benefits following washing. A comparison of some inventive advantages over a composition with another prior art activator is summarized by the data of Table 2.

TABLE 2

|  | Whiteness (Unit change with UV Filter) | Fluorescence (Unit change without UV Filter) |
|---|---|---|
| Inventive Composition |  |  |
| MMA Activator | 1.72 | 2.10 |
| Prior Art Composition |  |  |
| NM4CP Activator | 0.49 | -0.04 |

The MMA activator was the inventive N-methyl morpholinium acetonitrile methyl sulfate. The prior art "NM4CP" activator was N-methyl-4-cyanopyridinium methyl sulfate. Each composition included 20 ppm active oxygen.)

As shown by the data of Table 2 (more fully described in Example 6), the inventive composition provided substantial whiteness and whitening by comparison to a prior art composition which caused unacceptable fabric yellowing. The novel composition delivered its brightening and whitening benefit without negatively affecting fluorescent whitening agents.

Delivery Systems

The activators can be incorporated into a liquid or solid matrix for use in liquid or solid detergent bleaches by dissolving into an appropriate solvent or surfactant or by dispersing onto a substrate material, such as an inert salt (e.g., NaCl, $Na_2SO_4$) or other solid substrate, such as zeolites, sodium borate, or molecular sieves. Thus, activators of the invention can be dispersed onto a solid or granulated carrier such as silica, clay, zeolite, polymer, hydrogel, starch, or ion exchange material. Alternatively, solid activator can be encapsulated such as into waxes or polymers.

Surfactants with which the activators and active oxygen compositions may be combined or admixed include linear ethoxylated alcohols, such as those sold by Shell Chemical Company under the brand name Neodol. Other suitable nonionic surfactants can include other linear ethoxylated alcohols with an average length of 6 to 16 carbon atoms and averaging about 2 to 20 moles of ethylene oxide per mole of alcohol; linear and branched, primary and secondary ethoxylated, propoxylated alcohols with an average length of about 6 to 16 carbon atoms and averaging 0–10 moles of ethylene oxide and about 1 to 10 moles of propylene oxide per mole of alcohol; linear and branched alkylphenoxy (polyethoxy) alcohols, otherwise known as ethoxylated alkylphenols, with an average chain length of 8 to 16 carbon atoms and averaging 1.5 to 30 moles of ethylene oxide per mole of alcohol; and mixtures thereof.

Further suitable nonionic surfactants may include polyoxyethylene carboxylic acid esters, fatty acid glycerol esters, fatty acid and ethoxylated fatty acid alkanolamides, certain block copolymers of propylene oxide and ethylene oxide, and block polymers or propylene oxide and ethylene oxide with propoxylated ethylene diamine. Also included are such semi-polar nonionic surfactants like amine oxides, phosphine oxides, sulfoxides and their ethoxylated derivatives.

Anionic surfactants may also be suitable. Examples of such anionic surfactants may include the ammonium, substituted ammonium (e.g., mono-di-, and triethanolammonium), alkali metal and alkaline earth metal salts of $C_6$–$C_{20}$ fatty acids and rosin acids, linear and branched alkyl benzene sulfonates, alkyl sulfates, alkyl ether sulfates, alkane sulfonates, alpha olefin sulfonates, hydroxyalkane sulfonates, fatty acid mono glyceride sulfates, alkyl glyceryl ether sulfates, acyl sarcosinates and acyl N-methyltaurides.

Suitable cationic surfactants may include the quaternary ammonium compounds in which typically one of the groups linked to the nitrogen atom is a $C_{12}$–$C_{18}$ alkyl group and the other three groups are short chained alkyl groups which may bear inert substituents such as phenyl groups.

Suitable amphoteric and zwitterionic surfactants containing an anionic water-solubilizing group, a cationic group or a hydrophobic organic group include amino carboxylic acids and their salts, amino dicarboxylic acids and their salts, alkyl-betaines, alkyl aminopropylbetaines, sulfobetaines, alkyl imidazolinium derivatives, certain quaternary ammonium compounds, certain quaternary phosphonium compounds and certain tertiary sulfonium compounds.

Other common detergent adjuncts may be added if a bleach or detergent bleach product is desired. If, for example, a dry bleaching and cleaning composition is desired, the following ranges (weight %) appear practicable:

| 0.5–50.0% | Active Oxygen Source |
| 0.05–25.0% | Activator |
| 1.0–50.0% | Surfactant |
| 1.0–50.0% | Buffer |
| 5.0–99.9% | Filler, stabilizers, dyes, fragrances, briqhteners, etc. |

An example of a practical execution of a liquid delivery system is to dispense separately metered amounts of the activator (in some non-reactive fluid medium) and liquid hydrogen peroxide in a container such as described in Beacham et al., U.S. Pat. No. 4,585,150, issued Apr. 29, 1986. Such a dual bottle is contemplated for applications such as hard surface cleaners. It should also be understood that liquid formulations of the invention can have activator and a source of active oxygen present together so long as the pH of the solution is maintained in an acidic region, preferably between pH 0 and 4. Such a liquid formulation is storage stable. In order for activation to occur during use, such a liquid formulation will have the solution in or changed to an alkaline range, preferably a pH of about 8 to 11, and most preferably a pH of 9.5 to 11. In laundry use, this can automatically be achieved by adding such a liquid formulation to the wash, with activation occurring due to the presence of detergent as a source of alkalinity.

To summarize the single container and dual container delivery embodiments, a single container may include acetonitrile activator, surfactant, active oxygen source, and an acidic buffer (in order to stabilize the acetonitrile activator and the oxygen source (if hydrogen peroxide)). The liquid in which the just described components will be dispersed will sometimes be referred to as a "liquid matrix." This liquid matrix will include liquid (typically water) and remaining desired components such as whiteners, fragrances, colorants, stabilizers, preservatives, ionic strength adjuster, and the like. In a dual delivery embodiment, there may be one chamber containing the just described single container composition while the other chamber holds an alkaline solution. These two liquids could be combined in a third, mixing chamber of a trigger sprayer or other dispenser, or could be co-delivered to a selected site, for example, as two directed fluid streams (via a pump or trigger sprayer device) to a stain on a fabric, as in a "prewash" execution, or a stain on a hard surface. In another second dual delivery embodiment, it is the source of active oxygen that is contained in a second container until the two are combined for use. A third dual delivery embodiment can have the source of active oxygen and alkaline buffer in the one container and the acetonitrile activator, surfactant, and liquid matrix in the other. Other multiple delivery options are possible.

Compositions of the invention, when combined with a source of active oxygen, preferably function for bleaching best at an alkaline pH, but are shelf-stabilized best at an acidic pH. Thus, compositions of the invention preferably include buffer (admixed or in a separate container) which will either be acidic, alkaline, or both, depending upon whether the delivery system is single or double. In selecting a buffer to provide an acidic pH, a mineral acid such as HCl, sulfuric, nitric, phosphoric, sulfonic, methyl sulfuric, or organic such as citric, oxalic, glutaric, acetic, benzene sulfonic, etc., are well known to the art. The alkaline buffer may be selected from sodium carbonate, sodium bicarbonate, sodium borate, sodium silicate, phosphoric acid salts, and other alkali metal/alkaline earth metal salts known to those skilled in the art. Organic buffers, such as succinates, maleates and acetates may also be suitable for use. When the composition is ready for use, it is especially advantageous to have an amount of alkaline buffer sufficient to maintain a pH greater than about 8, more preferably in the range of about 8.5 to about 10.5 for most effective bleaching.

Compositions of the invention will typically include a filler material, which in solid (e.g. granulated) compositions of the invention can be viewed as forming all or part of a matrix where the nitrile is carried by or encapsulated in the solid matrix. The filler material (which may actually constitute the major constituent by weight) is usually sodium sulfate. Sodium chloride is another potential filler.

Other adjuncts (useful in cleaning and laundering applications) are optionally included in the inventive compositions. Dyes include anthraquinone and similar blue dyes. Pigments, such as ultramarine blue (UMB), may also be used, and can have a bluing effect by depositing on fabrics washed with a detergent bleach containing UMB. Monastral colorants are also possible for inclusion. Brighteners or whiteners, such as stilbene, styrene and styrylnaphthalene brighteners (fluorescent whitening agents), may be included. Fragrances used for aesthetic purposes are commercially available from Norda, International Flavors and Fragrances and Givaudon. Stabilizers include hydrated salts, such as magnesium sulfate, and boric acid.

In some of the compositions herein, adjuvants include (and are especially preferred) a chelating agent or sequestrant, most preferably, an aminopolyphosphonate. These chelating agents assist in maintaining the solution stability of the activators and active oxygen source in order to achieve optimum performance. In this manner, they are acting to chelate heavy metal ions, which cause catalyzed decomposition of the (believed) in situ formed peroxyimidic acids, although this is a non-binding theory of their action and not limiting.

The chelating agent is selected from a number of known agents which are effective at chelating heavy metal ions. The chelating agent should be resistant to hydrolysis and rapid oxidation by oxidants. Preferably, it should have an acid dissociation constant ($pK_a$) of about 1–9, indicating that it dissociates at low pH's to enhance binding to metal cations. Acceptable amounts of the (optional) chelating agent range from 0–1,000, more preferably 5–500, most preferably 10–100 ppm chelating agent, in the wash liquor.

The most preferred chelating agent is an aminopolyphosphonate, which is commercially available under the trademark Dequest from Monsanto Company. Examples thereof are Dequest 2000, 2041, and 2060. (See also Bossu U.S. Pat. No. 4,473,507, column 12, line 63 through column 13, line 22, incorporated herein by reference.) A polyphosphonate, such as Dequest 2010, is also suitable for use.

Other chelating agents, such as ethylenediaminetetraacetic acid (EDTA) and nitrilotri-acetic acid (NTA) may also be suitable for use. Still other new, preferred chelating agents are new propylenediaminetetraacetates, such as Hampshire 1,3 PDTA, from W. R. Grace, and Chel DTPA 100#F, from Ciba-Geigy A. G. Mixtures of the foregoing may be suitable.

Additional desirable adjuncts are enzymes (although it may be preferred to also include an enzyme stabilizer). Proteases are one especially preferred class of enzymes. They are preferably selected from alkaline proteases. The term "alkaline," refers to the pH at which the enzymes' activity is optimal. Alkaline proteases are available from a wide variety of sources, and are typically produced from various microorganism (e.g., *Bacillus subtilisis*). Typical examples of alkaline proteases include Maxatase and Maxacal from International BioSynthetics, Alcalase, Savinase, and Esperase, all available from Novo Industri A/S. See also Stanislowski et al., U.S. Pat. No. 4,511,490, incorporated herein by reference.

Further suitable enzymes are amylases, which are carbohydrate-hydrolyzing enzymes. It is also preferred to include mixtures of amylases and proteases. Suitable amylases include Rapidase, from Société Rapidase, Milezyme from miles Laboratory, and Maxamyl from International BioSynthetics.

Still other suitable enzymes are cellulases, such as those described in Tai, U.S. Pat. No. 4,479,881, Murata et al., U.S. Pat. No. 4,443,355, Barbesgaard et al., U.S. Pat. No. 4,435,307, and Ohya et al., U.S. Pat. No. 3,983,082, incorporated herein by reference.

Yet other suitable enzymes are lipases, such as those described in Silver, U.S. Pat. No. 3,950,277, and Thom et al., U.S. Pat. No. 4,707,291, incorporated herein by reference.

The hydrolytic enzyme should be present in an amount of about 0.01–5%, more preferably about 0.01–3%, and most preferably about 0.1–2% by weight of the detergent. Mixtures of any of the foregoing hydrolases are desirable, especially protease/amylase blends.

Anti-redeposition agents, such as carboxymethylcellulose, are potentially desirable. Foam boosters, such as appropriate anionic surfactants, may be appropriate for inclusion herein. Also, in the case of excess foaming resulting from the use of certain surfactants, anti-foaming agents, such as alkylated polysiloxanes, e.g. dimethylpolysiloxane, would be desirable.

Applications

Compositions of the invention are useful as or in laundry products, such as bleaching additives, detergents, detergent boosters, detergents with bleach, bleaches, bleaching aids, stain removers, and spot treatment products such as stain removers, prewash and presoak laundry aids. Among the advantages derived from compositions of the invention are improved cleaning, stain removal, spot removal, whitening, and brightening of treated articles.

Further benefits from use of the inventive compositions include scavenging of free dye during laundering to prevent dye transfer between garments (sometimes known as dye transfer inhibition).

Other product applications include household cleaning products, such as hard surface cleaners either for direct use or to be diluted with water prior to use. Exemplary surface cleaners are tile and grout cleaners, bathroom (floor, toilet, and counter) and kitchen (floor, sink, and counter) cleaners. Additionally, kitchen products such as dishwasher detergents with bleach or bleach cleaning and scrubbing pads are contemplated. Among the benefits derived from use of the inventive compositions in such applications are improved stain and spot removal and general cleaning of the treated surfaces to remove food, rust, grime, mildew, mold, and other typical stains found on such surfaces.

Additionally, non-household product applications are contemplated where an effective level of active oxygen generated in situ to treat water is useful. Illustrative of such applications are pool and spa additives, as well as cleaners to remove stains on outdoor concrete, stucco, siding, wood and plastic surfaces.

Aspects of the invention will now be illustrated by the following examples. Example 1 (with subparts 1A–1D) illustrates preparation of embodiments having Formula II structures. Example 2 (with subparts 2A and 2B) illustrates preparation of embodiments having the Formula IB structure. Examples 3–7 illustrate various aspects and properties of the invention. It will be understood that these examples are intended to illustrate, and not to limit, the invention.

EXAMPLE 1

In general, N-quaternary acetonitrile compounds are readily prepared from N-acetonitrile precursors by employing selected alkyl halides and using well-known synthetic approaches, such as are described by Menschutkin, Z. Physik. Chem., 5, 589 (1890), and Z. Physik. Chem., 6, 41 (1890); Abraham, Progr. Phys. Org. Chem., 11, 1 (1974); and Arnett, J. Am. Chem. Soc., 102, 5892 (1980).

Specifically detailed preparations of four preferred embodiments are described below as illustrative.

EXAMPLE 1A

Preparation of N-Methyl Morpholinium Acetonitrile (MMA)

To a solution of 30 g of morpholine acetonitrile in 75 ml of ethyl acetate was added 22.5 ml of dimethyl sulfate, corresponding to approximately equivalent molar amounts of the two reagents. The resulting solution was mechanically stirred in an oil bath maintained at 40° C. After 10 minutes of stirring, a semi-solid precipitate having a brownish coloration formed and settled on the bottom of the flask. HPLC (high pressure liquid chromatography) analysis showed at least 4 undesirable side products, which were removed. The remaining solution was again heated to 40° C. and reacted for an additional 16 hours. After this time, the resulting white paste was filtered and washed with ethyl acetate. MMA was isolated after drying this filtrate as a free flowing off-white solid in 79% yield, having a melting point of 99–101° C. The purity of the MMA was determined by HPLC to be greater than 95%.

EXAMPLE 1B

Preparation of N-Hexyl Morpholinium Acetonitrile (HMA)

Combined were 44.08 g of hexylbromide, 29.88 g morpholine, and 28.0 g anhydrous sodium carbonate with 150 ml of acetone in a large round bottom flask. This mixture was refluxed for 8 hours at the boiling point of acetone or approximately 60° C., then cooled to room temperature and the solid sodium carbonate filtered. Acetone was removed using a roto-evaporator. The resulting oil was dissolved in ether and washed twice with water and once with brine solution. The ether solution was dried over anhydrous sodium sulfate. After filtering, ether was removed in-vacuo leaving 45.2 g of a lightly-colored oil in 98.8% yield. Gas chromatography showed the oil to be N-hexyl morpholine in approximately 95% purity. Combined were 2.0 g of N-hexylmorpholine with 0.95 g of chloroacetonitrile in a small vial. After capping the vial was heated to 55° C. for approximately 24 hours. A viscous oil resulted which solidified upon addition of a small amount of ethylacetate. The solid was filtered and washed with excess ethylacetate, then dried in a vacuum dessicator resulting in 2.3 g of final white solid, in a yield of approximately 84%. Carbon-13 NMR analysis revealed the desired product present with no other detectable impurities noted.

EXAMPLE 1C

Preparation of N-Octyl Morpholinium Acetonitrile (OMA)

Combined were 51.5 g of octylbromide, 29.88 g morpholine, and 28.0 g anhydrous sodium carbonate with 150 ml of acetone in a large round bottom flask. This mixture was refluxed for 8 hours at the boiling point of acetone or approximately 60° C., then cooled to room temperature and the solid sodium carbonate filtered. Acetone was removed using a roto-evaporator. The resulting oil was dissolved in ether and washed twice with water and once with brine solution. The ether solution was dried over anhydrous sodium sulfate. After filtering, ether was removed in-vacuo, leaving a slightly-colored oil. Gas chromatography showed the oil to be N-octyl morpholine, obtained with a yield of 98% and having greater than 95% purity. Combined were 2.3 g of N-octyl morpholine together with 1.0 g of chloroacetonitrile in a small vial. After capping the vial was heated to 55° C. for approximately 24 hours. A viscous oil resulted which solidified upon addition of a small amount of ethylacetate. The solid was filtered and washed with excess ethylacetate, then dried in a vacuum dessicator resulting in the isolation of a white solid, in a yield of approximately 84%. Carbon-13 NMR analysis revealed the desired product present with no other detectable impurities noted.

EXAMPLE 1D
Preparation of N-Butyl Morpholinium Acetonitrile (BMA)

Combined were 10 g of butylbromide, 6.36 g morpholine, and 28.0 g anhydrous sodium carbonate with 150 ml of acetone in a large round bottom flask. This mixture was refluxed for 8 hours at the boiling point of acetone or approximately 60° C., then cooled to room temperature and the solid sodium carbonate filtered. Acetone was removed using a roto-evaporator. The resulting oil was dissolved in ether and washed twice with water and once with brine solution. The ether solution was dried over anhydrous sodium sulfate. After filtering, ether was removed in-vacuo leaving 5.15 g of product estimated at 49.3% yield. Gas chromatography showed the product to be N-butyl morpholine in approximately 95% purity. Combined 7.2 g of N-butyl morpholine together with 3.0 ml of chloroacetonitrile in a small vial. After capping the vial was heated to 60° C. for approximately 24 hours. An oil resulted which solidified upon addition of a small amount of ethylacetate. The solid was filtered and washed with excess ethylacetate, then dried in a vacuum dessicator resulting in a white solid in nearly stoichiometric yield. Carbon-13 NMR analysis revealed the desired product present with no other detectable impurities noted.

EXAMPLE 2

Dimer embodiments of the invention, for example such as illustrated by Formula IB, may be prepared as follows.

EXAMPLE 2A
1,6-Bis(4-cyanomethylmorpholinium)hexane Dichloride (HDMMA)

100 ml of morpholine (1.147 mole) and 150 ml ethylacetate (EtOAc) were added to 500 ml Morton flask equipped with ref lux condenser, thermometer, mechanical stirrer, and heating mantel. 25 ml of 1,6-dichlorohexane (0.172 mole) was added slowly to flask at room temperature. This was refluxed for 48 hours. Gas chromatogram showed 90% completion of the reaction. The product 1,6-bismorpholinohexane was purified from reaction mixture by vacuum filtration to remove the morpholine hydrochloride, and the light yellow filtrate was purified by adsorption chromatography. $^{13}$C NMR showed a spectrum consistent with structure with very minor impurities. Gas chromatography showed an approximate purity of 98.2% based upon peak areas. The collected amount of 1,6-bismorpholinehexane was 30.0 g, which corresponds to a yield of 66.6%.

12.68 g of bismorpholinohexane (0.049 mole) and 55 ml EtOAc were added to 500 ml Morton flask equipped with reflux condenser, pressure equalizing dropping funnel, mechanical stirrer, and heating mantel. 15 ml of chloroacetonitrile (0.238 mole) was added slowly to flask at room temperature. This was refluxed for 5 hours. Light brown solid precipitated from the solution, and the solid was isolated by vacuum filtration, rinsed with EtOAc, and dried overnight in vacuum oven at ambient temperature. $^{13}$C NMR showed a spectrum consistent with structure with a significant, but small impurity of starting amine. Collected 12.6 g of product, corresponding to 57.1% yield from this step.

EXAMPLE 2B
1,2-Bis(2-(4-cyanomethylmorpholinium)ethoxy)ethane Dichloride (EODMMA)

100 ml of morpholine (1.147 mole) and 150 ml EtOAc were added to 500 ml Morton flask equipped with reflux condenser, thermometer, mechanical stirrer, and heating mantel. 25 ml of 1,2-bis(2-chloroethoxy)ethane (0.160 mole) added slowly to flask at room temperature. This was refluxed for 16 hours. Product 1,2-bis(2-morpholinoethoxy) ethane was purified from reaction mixture by vacuum filtration to remove the morpholine hydrochloride, and the light yellow filtrate was purified by adsorption chromatography. 18.4 g of product was collected, and a gas chromatogram showed an approximate purity of 98.2% based upon peak areas. The collected amount of 1,2-bis(2-morpholinoethoxy)ethane corresponds to a yield of 39.2%.

14.94 g of 1,2-bis(2-morpholinoethoxy)ethane (0.051 mole) and approximately 100 ml EtOAc were added to 500 ml Morton flask equipped with reflux condenser, pressure equalizing dropping funnel, mechanical stirrer, and heating mantel. 25 ml of chloroacetonitrile (0.397 mole) was added slowly to flask at room temperature. This was refluxed for 8 hours. Light brown solid precipitated from the solution, and the solid was very tacky and stiff. The mechanical stirrer froze solid in the material. Mother liquor was decanted off the solid, and the solid was redissolved in methanol. The solvent was evaporated in a recrystallization dish for several days. Mother liquor reacted further for an additional 8 hours without any stirring, with more product forming. The product from the second heating was collected in a manner identical to first. 14.6 g of product was collected from the first reaction period and 5.5 g from the second reaction period. Together the two reactions yielded 20.1 g of product, corresponding to 85.4% yield. $^{13}$C NMR shows spectrum consistent with the proposed structure with a small impurity of methanol.

EXAMPLE 3

Compounds with the Formula I or Formula III structure are particularly contemplated as activators in bleaching applications. Therefore, a desired property of these compounds is that of exhibiting perhydrolysis when combined with hydrogen peroxide. As summarized by the data in Table 3, titrated perhydrolysis yields with excess hydrogen peroxide present (as determined by electrochemical analyzer with response standardized against oxone or peroxide standard solution) were performed for six preferred embodiments of the invention.

TABLE 3

| Name | Titrated % Yield |
| --- | --- |
| N-Methyl Morpholinium Acetonitrile Methyl Sulfate (MMA) | 46 |
| N-Hexyl Morpholinium Acetonitrile Chloride (HMA) | 55 |
| N-Octyl Morpholinium Acetonitrile Chloride (OMA) | 42 |
| N-Methyl-piperazinium-N,N, diacetonitrile Methyl Sulfate (MPDA) | 31.5 |
| 1,6-di(4-Cyanomethyl-morpholinium)hexane Dichloride (HDMMA) | 40 |
| 1,2-bis(2-(4-Cyanomethyl-morpholinium)ethoxy)ethane dichloride (EODMMA) | 20 |

We believe that the acetonitrile moiety is necessary for the perhydrolysis activity, since a compound analogous to MMA, but with a proprionitrile moiety instead of the acetonitrile moiety, was shown to have no perhydrolysis yield when tested at pH 10.

Bleaching compositions of the invention include a source of active oxygen. The source of active oxygen itself constitutes a bleaching agent; however, bleaching compositions of the invention that include the Formula I or Formula III nitrites as activators, together with a source of active oxygen, provide enhanced bleaching with respect to the oxygen source by itself. This is demonstrated by Examples 3A and 3B.

EXAMPLE 3A

In a commercial washing machine (with scoured ballast) garments were split and washed in either of two treatments. Wash conditions were warm water (93° F.) using No-P Grease Release Tide (65 g) in a 69 L washer, 1 min. premix time with 12 minute wash, cold water (68° F.) rinse with 100 ppm hardness as $Ca^{2+}$:$Mg^{2+}$ (3:1).

The two treatments were either (1) Clorox 2 Colorbright (76.2 g) delivering 18 ppm A.O. (theoretical active oxygen) as sodium perborate (7.75 g), and a wash pH between 10.5–10.6; or (2) an inventive bleaching composition, but additionally containing 12 ppm A.O. as MMA (13.05 g-active) and 28 ppm A.O. as sodium perborate (12.05 g) and sodium bicarbonate substituted in part for sodium carbonate to achieve a wash water pH between 10.0–10.1. Both treatments also contained Dequest 2006 at an active level of 0.69 g added in a 69 L wash volume. 40 split garment halves and socks were visually judged in a blind side-by-side panel to compare treatment differences, as shown by Table 4.

TABLE 4

| Garment/Evaluation | Mean Score | Standard Error | Confidence Level | Winner at 95% Confidence Level |
|---|---|---|---|---|
| Socks/Cleaning | 0.49 | 0.22 | 96.96 | Inventive bleaching composition with MMA |
| Dress Shirt Color/Cleaning | 0.33 | 0.13 | 98.56 | Inventive bleaching composition with MMA |
| T-Shirt/Whiteness | 0.53 | 0.19 | 99.00 | Inventive bleaching composition with MMA |

The mean score reported in Table 4 is the average of all judges' responses on a scale of −4 to +4, evaluating either overall cleaning or whiteness differences between halves or matched pairs (socks).

As is demonstrated by the data of Table 4 above, the inventive bleaching composition (with MMA as activator) showed superior bleaching to perborate bleach alone on various soiled consumer garments.

EXAMPLE 3B

A commercial washing machine was used with scoured ballast. Wash conditions were warm wash (98° F.) using No-P Grease Release Tide (65 g) in a 69 L washing, 1 min. premix time with 12 minute wash, cold water (68° F.) rinse with 100 ppm hardness at $Ca^{2+}$:$Mg^{2+}$ (3:1). Treatments included enzyme (Savinase 6T-0.83 g), whitener speckles containing Blankophor HRS (1.71 g), metal sequestrant (Dequest 2006—1.73 g/69 L) and one of three sodium carbonate/sodium bicarbonate mixtures to achieve desired wash water pH: pH 10.5—11.9 g NaCl and 55.6 g $Na_2CO_3$; pH 10.0—40.5 g $Na_2CO_3$ and 27 g $Na_2HCO_3$; pH 9.5—13.5 g $Na_2CO_3$ and 54 g $Na_2HCO_3$, all weight added per single 69 L wash volume to maintain equivalent ionic strength.

TABLE 5

| | % Stain Removal Relative to Wash with Control Detergent Wash | | |
|---|---|---|---|
| | Tea | Fountain Pen Ink | 8-Stain Average |
| Inventive Compositions | | | |
| 1 (pH 10.5, 4 ppm MMA, 18 ppm A.O.) | 25 | 23 | 11 |
| 2 (pH 9.5, 8 ppm MMA, 18 ppm A.O.) | 19 | 30 | 9 |
| 3 (pH 10.5, 8 ppm MMA, 18 ppm A.O.) | 25 | 30 | 10 |
| 4 (pH 10.0, 8 ppm MMA, 18 ppm A.O.) | 27 | 32 | 9 |
| 5 (pH 10.5, 12 ppm MMA, 28 ppm A.O.) | 31 | 33 | 14 |
| 6 (pH 10.5, 16 ppm MMA, 36 ppm A.O.) | 38 | 37 | 16 |
| Comparative Composition | | | |
| (pH 10.5, 18 ppm A.O.) | 15 | 1 | 6 |

As is shown by the data of Table 5 above, six compositions of the invention (with the inventive MMA activator) performed substantially better in removing tea stains than the comparative perborate, and removed fountain pen ink stain 20 to almost 40 times better than the perborate. Over an eight stain average (including grass, coffee, tea, gravy, grape, spaghetti, berry, and mustard) the inventive bleaching compositions were consistently better than the comparative perborate at bleaching. The data are differences in stain removal versus the no-P Tide wash.

EXAMPLE 4

This example illustrates the substantial bleaching (cleaning and stain removal) benefits on common laundry stains of several different inventive compositions when used as a laundry additive with respect to use of detergent alone and with respect to use of the detergent plus hydrogen peroxide source alone.

Single 12 minute washes in No-P Ultra Tide detergent (0.95 g/L) at 98° F. were followed by a 1 minute cold water rinse. All washes contained 100 ppm hardness ions ($Ca^{2+}$:$Mg^{2+}$ at 3:1), sodium bicarbonate/sodium carbonate mixture (0.364 g/L and 0.545 g/L, respectively) to adjust wash water to approximately pH 10, and Dequest 2006 at 0.026 g/L. Wash volume was 1.5 liters with agitation at 150 ppm using a six-well Terg-o-tometer. Stains were made on 100% cotton using common food and stain ingredients: coffee, tea, grape, berry, ball point pen ink (BPI) and fountain pen ink (FPI). One standard stained flag containing all stains and six clean cotton swatches for ballast were washed per well. Stain removal was measured photometrically by determining delta SR(e) from colorimeter readings before and after washing. Level of oxidant is theoretical % active oxygen in ppm (ppm A.O.) based on formula weight and number of equivalents. Peroxide ($H_2O_2$) was supplied in the form of sodium perborate monohydrate, where 0.156 g/L corresponds to 25 ppm active oxygen (AO) in the Terg-o-tometer.

TABLE 6

| | % S.R. | | | |
|---|---|---|---|---|
| | Tea | Grape | Fountain Pen Ink | 6-Stain Average |
| Inventive Compositions: | | | | |
| 7 (10 ppm MMA, 25 ppm A.O.) | 47.7 | 84.1 | 83.2 | 79.1 |
| 8 (10 ppm HMA, 25 ppm A.O.) | 37.4 | 81.6 | 78.9 | 76.8 |
| 9 (10 ppm OMA, 25 ppm A.O.) | 34.4 | 81.3 | 75.5 | 75.6 |
| 10 (10 ppm MPPA, 25 ppm A.O.) | 41.9 | 84.8 | 82.9 | 78.6 |
| 11 (10 ppm MPA*, 25 ppm A.O.) | 42.9 | 80.0 | 80.8 | 77.0 |
| Control Compositions: | | | | |
| Detergent only | 31.4 | 63.4 | 52.1 | 61.1 |
| Peroxide and Detergent (25 ppm A.O.) | 32.5 | 64.9 | 51.0 | 63.2 |

*N-methyl piperidinium acetonitrile methyl sulfate

As seen by the data of Table 6 above, all the inventive compositions provided improved cleaning and stain removal with respect to the detergent only control composition and with respect to the peroxide and detergent control composition.

EXAMPLE 5

This example again demonstrates the excellent bleaching (cleaning and stain removal) benefit of inventive compositions and also serves to compare two of the inventive embodiments with a prior art composition where the nitrile activator has an aromatic ring. This prior art bleaching composition is N-acetonitrile pyridinium chloride ("PYACN") as the activator.

All treatments were duplicated 12 minutes in No-P Ultra Tide detergent with Cellulase (1.53 g/1.5 L) at 96° F., followed by 1 minute cold water rinse. All washes contained 100 ppm hardness ($Ca^{2+}$:$Mg^{2+}$ at 3:1). Wash volume was 1.5 liters with agitation at 150 ppm using a six-well Terg-o-tometer. Stains were made using a SAM (Stain Application Machine) on 100% cotton using common food stain ingredients: grass, coffee, tea, grape, spaghetti, mustard, berry, and fountain pen ink (FPI). Two standard stained flags containing all stains and six clean cotton swatches for ballast were washed per well. Stain removal was measured photometrically by determining delta SR(e) from calorimeter readings before and after washing. Level of oxidant was theoretical % active oxygen in ppm (ppm A.O.) based on formula weight and number of equivalents. Peroxide ($H_2O_2$) was supplied in the form of hydrogen peroxide by adding 0.11 ml of 30% stock to 1.5 L wash volumes to give the equivalent of 25 ppm active oxygen (AO) in the Terg-o-tometer.

TABLE 7

| | % S.R. | | | |
|---|---|---|---|---|
| | Tea | Grape | Fountain Pen Ink | 8-Stain Average |
| Inventive Compositions: | | | | |
| 12 (12 ppm MMA, 25 ppm A.O.) | 54.6 | 73.4 | 80.2 | 72.4 |
| 13 (12 ppm BMA, 25 ppm A.O.) | 51.2 | 76.4 | 77.1 | 73.6 |
| Comparative Composition | | | | |
| (12 ppm PYACN, 25 ppm A.O.) | 42.0 | 65.2 | 63.1 | 63.2 |
| Control Compositions | | | | |
| Detergent only | 34.8 | 54.8 | 49.7 | 65.9 |
| Detergent and 25 ppm A.O. | 39.6 | 57.9 | 51.9 | 67.1 |

As shown by the Table 7 data above, both inventive composition embodiments clearly outperformed the comparative bleaching composition.

EXAMPLE 6

These studies were conducted to determine whether embodiments of the invention would deliver their brightening and whitening benefit without negatively affecting fluorescent whitening agents that may already be present on clothing or be present simultaneously in the wash water during use. The "FWA" source was that present in the detergent used, or existing on the prebrightened cotton fabric obtained from Testfabrics, Inc. The wash study experiments also compared a prior art nitrile precursor (but with an aromatic ring) as to brightening (whiteness improvement due to bleaching) and whitening (lack of colored by-product formation). The prior art activator used for comparison was N-methyl-4-cyanopyridinium methylsulfate ("NM4CP").

All treatments contained No-P Tide (65.3 g/69 L), standard hardness (100 ppm of $Ca^{2+}$:$Mg^{2+}$), sodium bicarbonate (7.2 g) to adjust incoming wash water pH and an additional 20 g of sodium bicarbonate and 49 g of sodium carbonate to adjust final wash water pH to approximately 10. In addition, 1.73 g of Dequest 2006 and 9.36 g of sodium perborate monohydrate were added per 69 L. All treatments were done in conventional washing machines using a 12 minute wash cycle. Two pre-brightened cotton T-shirt swatches were attached to pillowcases and added to each washing machine in combination with 6 lbs. of clean ballast.

TABLE 8

| | Whiteness (Unit Change) | Fluorescence with UV Filter (Unit Change) |
|---|---|---|
| Inventive Composition: | | |
| 14 (8 ppm MMA, 20 ppm A.O.) | 3.82 | 2.10 |
| Comparative Composition: | | |
| (8 ppm NM4CP, 20 ppm A.O.) | 0.45 | −0.04 |
| Control Compositions: | | |
| Detergent only | 2.63 | 1.57 |
| Detergent and 20 ppm A.O. | 2.84 | 1.69 |

As shown by the data of Table 8 above, the inventive composition embodiment delivered its brightening and whitening benefit without negatively affecting the FWAs. By contrast, the comparative bleaching composition negatively affected the FWAS and caused unacceptable fabric yellowing, perhaps due to reactions pertaining to the aromatic ring of the prior art nitrile activator.

EXAMPLE 7

Four granulated compositions of the invention were formulated and tested for storage stability. Table 9A sets out the formulations, and Table 9B summarizes the percent remaining perhydrolysis activity after six weeks at 80% F storage (80% relatively humidity).

TABLE 9A

| | Inventive Composition No. | | | |
|---|---|---|---|---|
| Component | 15 Wt. % | 16 Wt. % | 17 Wt. % | 18 Wt. % |
| Activator (MMA) | 13.7 | 6.8 | 6.9 | 20.4 |
| Active Oxygen Source (Sodium Perborate Hydrate) | 8.8 | 9.2 | 9.2 | 7.8 |
| Buffer/(Sodium Carbonate) Filler | 71.0 | 74.5 | 74.5 | 63.3 |
| Builder (Polyacrylate) | 1.2 | 1.3 | 1.3 | 1.1 |
| Chelating Agent/Sequestrant | 0.8 | 0.8 | 0.8 | 0.7 |
| Filler/(Sodium Silicate) Buffer | 3.0 | 3.2 | 3.2 | 2.7 |
| Enzyme | 0 | 0.9 | 0.9 | 0.9 |
| Miscellaneous (color, whitener, etc.) | 1.5 | 3.3 | 3.2 | 3.1 |

TABLE 9B

| Inventive Composition Number | % Wt. Active MMA remaining |
|---|---|
| 15 | 100 |
| 16 | 74 |
| 17 | 100 |
| 18 | 86 |

As shown by the data of Table 9B, the inventive composition embodiments exhibited good storage stability.

It is to be understood that while the invention has been described above in conjunction with preferred specific embodiments, the description and examples are intended to illustrate and not limit the scope of the invention, which is defined by the scope of the appended claims.

It is claimed:

1. A compound having the structure of Formula IA

FORMULA IA

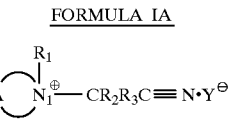

wherein A is a saturated ring formed by a plurality of atoms in addition to the $N_1$ atom, the saturated ring atoms to include at least one carbon atom and at least one heteroatom in addition to the $N_1$ atom, the said one heteroatom selected from the group consisting of O, S and N atoms, the substituent $R_1$ bound to the $N_1$ atom of the Formula IA structure is (a) a $C_{1-8}$ alkyl or alkoxylated alkyl where the alkoxy is $C_{2-4}$, (b) a $C_{4-24}$ cycloalkyl, (c) a $C_{7-24}$ alkaryl, (d) a repeating or nonrepeating alkoxy or alkoxylated alcohol, where the alkoxy unit is $C_{2-4}$, in Formula IA at least one of the $R_2$ and $R_3$ substituents is H and the other of $R_2$ and $R_3$ is H, a $C_{1-24}$ alkyl, cycloalkyl, or alkaryl, or a repeating or nonrepeating alkoxyl or alkoxylated alcohol where the alkoxy unit is $C_{2-4}$, and Y is substantially any inorganic or organic anion.

* * * * *